(12) United States Patent
Tachikawa

(10) Patent No.: US 11,213,271 B2
(45) Date of Patent: Jan. 4, 2022

(54) RADIATION IMAGING SYSTEM, INFORMATION TERMINAL, RADIATION IMAGING METHOD, AND COMPUTER-READABLE STORAGE MEDIUM

(71) Applicant: CANON KABUSHIKI KAISHA, Tokyo (JP)

(72) Inventor: Hirohide Tachikawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 42 days.

(21) Appl. No.: 16/528,989

(22) Filed: Aug. 1, 2019

(65) Prior Publication Data

US 2019/0350551 A1 Nov. 21, 2019

Related U.S. Application Data

(63) Continuation of application No. PCT/JP2018/003489, filed on Feb. 1, 2018.

(30) Foreign Application Priority Data

Feb. 8, 2017 (JP) .............................. JP2017-021559

(51) Int. Cl.
*A61B 6/00* (2006.01)

(52) U.S. Cl.
CPC .......... *A61B 6/5294* (2013.01); *A61B 6/4266* (2013.01); *A61B 6/464* (2013.01); *A61B 6/542* (2013.01)

(58) Field of Classification Search
CPC ....... A61B 6/00; A61B 6/4266; A61B 6/4405; A61B 6/464; A61B 6/5294; A61B 6/542; A61B 6/548; A61B 6/563
See application file for complete search history.

(56) References Cited

U.S. PATENT DOCUMENTS

| 2007/0103553 | A1 | 5/2007 | Hara |
| 2012/0049080 | A1 | 3/2012 | Enomoto |
| 2015/0117607 | A1* | 4/2015 | Hayashi .................. A61B 6/463 378/62 |

FOREIGN PATENT DOCUMENTS

| EP | 2865332 A1 | 4/2015 |
| JP | 2008119018 A | 5/2008 |

(Continued)

OTHER PUBLICATIONS

Japanese Office Action dated Nov. 10, 2020, for Corresponding Japanese Application No. 2017-021559.

(Continued)

*Primary Examiner* — Dani Fox

(74) *Attorney, Agent, or Firm* — Carter, DeLuca & Farrell LLP

(57) ABSTRACT

A radiation imaging system, including: a radiation imaging unit configured to perform radiation imaging and generate radiation image data based on detected radiation; and an image processing unit configured to perform first image processing on the radiation image data to generate a first image and capable of transmitting the first image to an information terminal, wherein the radiation imaging unit is configured to subject the radiation image data to second image processing to generate a second image and transmit the second image to the information terminal.

19 Claims, 11 Drawing Sheets

(56) References Cited

FOREIGN PATENT DOCUMENTS

| JP | 2013113616 A | 6/2013 |
|---|---|---|
| JP | 2015083026 A | 4/2015 |
| JP | 2015100404 A | 6/2015 |
| JP | 2016034470 A | 3/2016 |
| JP | 2016101210 A | 6/2016 |
| JP | 2016147044 A | 8/2016 |
| WO | 2006101231 A1 | 9/2006 |
| WO | 2012165171 A1 | 12/2012 |

OTHER PUBLICATIONS

Japanese Office Action dated Jan. 26, 2021, for Corresponding Japanese Application No. 2017-021559.
Korean Office Action dated Jan. 25, 2021, for Corresponding Korean Application No. 10-20197025496.
Office Action issued by the Federal Institute of Industrial Property of Russia dated Feb. 25, 2020 in corresponding RU Patent Application No. 2019128061, with English translation.
International Preliminary Report on Patentability issued by the International Bureau in corresponding International Application No. PCT/JP2018/003489 dated Aug. 22, 2019, with English translation.
International Search Report dated Apr. 17, 2018 in corresponding International Patent Application No. PCT/JP2018/003489.
Examination Report issued by the Intellectual Property Office of India dated Feb. 26, 2021 in corresponding IN Patent Application No. 201947034239, with English translation.
Decision of Refusal issued by the Japan Patent Office dated May 18, 2021 in corresponding JP Patent Application No. 2017-021559, with English translation.
Examination Report dated Oct. 15, 2021 by the GB Intellectual Property Office in corresponding GB Patent Application No. GB1910165.8.

\* cited by examiner

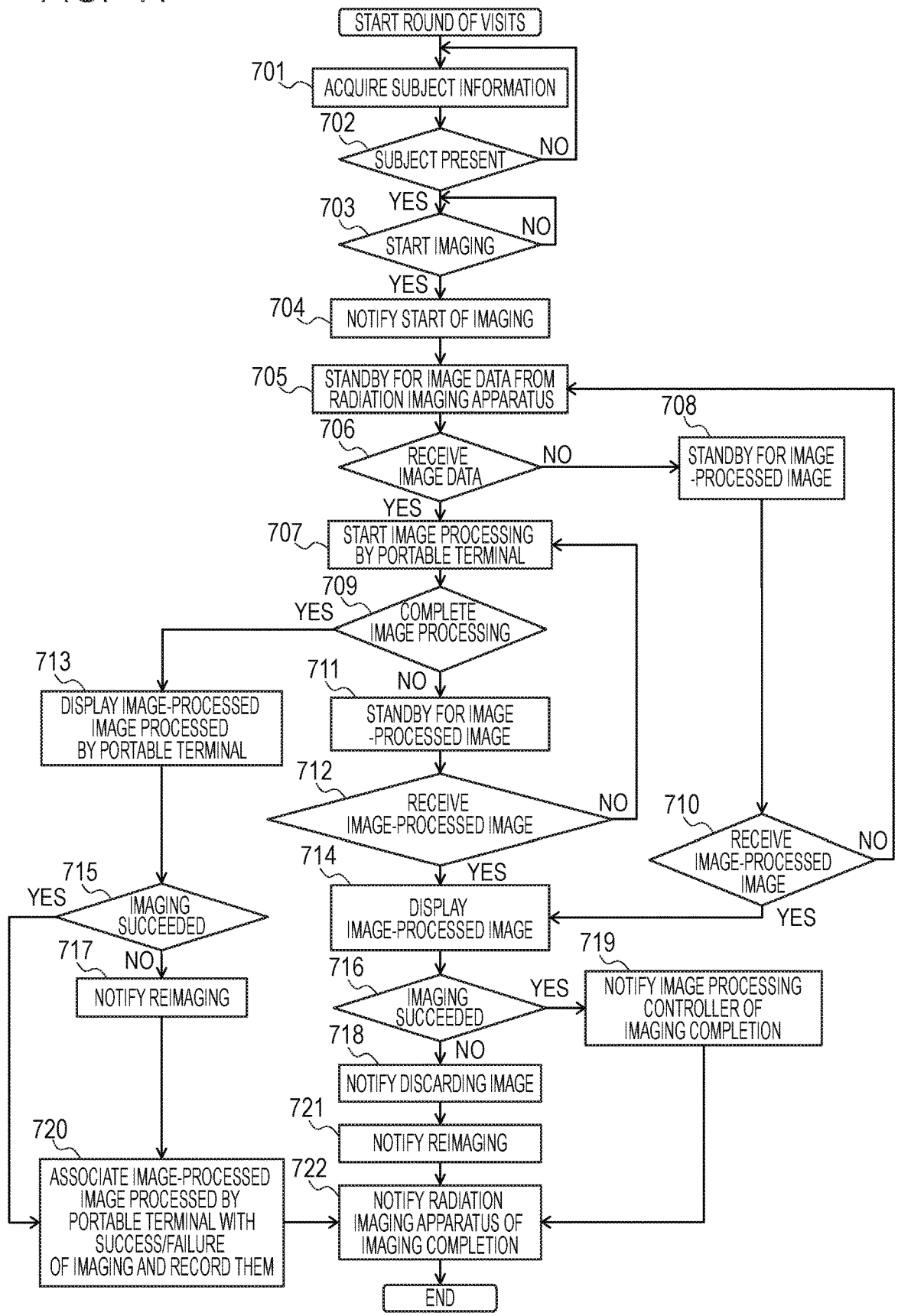

RADIATION IMAGING SYSTEM, INFORMATION TERMINAL, RADIATION IMAGING METHOD, AND COMPUTER-READABLE STORAGE MEDIUM

CROSS-REFERENCE TO RELATED APPLICATIONS

This application is a Continuation of International Patent Application No. PCT/JP2018/003489, filed Feb. 1, 2018, which claims the benefit of Japanese Patent Application No. 2017-021559, filed Feb. 8, 2017, both of which are hereby incorporated by reference herein in their entirety.

BACKGROUND OF THE INVENTION

Field of the Invention

The present invention relates to a radiation imaging system, an information terminal, a radiation imaging method, and a computer-readable storage medium.

Description of the Related Art

In a medical field, for example, in a case where a patient is subjected to radiation imaging for postoperative surveillance and the like, some conditions of the patient make it difficult to transfer the patient to an X-ray room. To deal with such a case, a medical trolley for radiation imaging, with which radiation imaging is performed in making rounds at sickrooms in a patients' hospital ward (hereinafter, referred to as a "medical trolley") or the like is often used. A typical medical trolley includes a radiation generating apparatus, a flat panel detector (FPD), an image processing controller, and a monitor connected to the image processing controller. A radiation image acquired by the FPD is transmitted to an image processing controller, subjected to image processing by the image processing controller, and displayed on a monitor.

In case where imaging is performed with a medical trolley, there has recently been a demand for reducing articles necessary in making rounds at sickrooms to perform the imaging efficiently. Hence, a radiation imaging system in which a portable terminal performing operation of radiation imaging and the like is used, and a radiation image subjected to image processing is transmitted to the portable terminal and displayed on the portable terminal is proposed. An operator can check the radiation image displayed on the portable terminal to determine success/failure of the radiation imaging.

However, in operation of a radiation imaging system with a conventional medical trolley, an FPD, an image processing controller, a portable terminal, an access point, and a LAN line work in cooperation to implement image processing of a radiation image, and the radiation image subjected to the image processing is displayed on the portable terminal.

Therefore, in a case where a malfunction occurs in the access point and the LAN line serving as a communication route, or in the image processing controller during capturing a radiation image, the radiation image subjected to the image processing is not transmitted to the portable terminal, or the transmission is delayed. In this case, an operator cannot check the radiation image subjected to the image processing on the portable terminal. In addition, if the operator cannot check the radiation image on the portable terminal, the operator cannot proceed to capturing a next radiation image.

SUMMARY OF THE INVENTION

A radiation imaging system according to an embodiment of the present invention is a radiation imaging system including: a radiation imaging unit configured to perform radiation imaging and generate radiation image data based on detected radiation; and an image processing unit configured to perform first image processing on the radiation image data to generate a first image and capable of transmitting the first image to an information terminal, wherein the radiation imaging unit is configured to subject the radiation image data to second image processing to generate a second image and transmit the second image to the information terminal.

Further features of the present invention will become apparent from the following description of exemplary embodiments with reference to the attached drawings.

BRIEF DESCRIPTION OF THE DRAWINGS

FIG. 11 is a flowchart illustrating operation of a portable terminal in the third embodiment.

DESCRIPTION OF THE EMBODIMENTS

Embodiments of the present invention will be described below in detail with reference to the accompanying drawings.

First Embodiment

Figure 1:
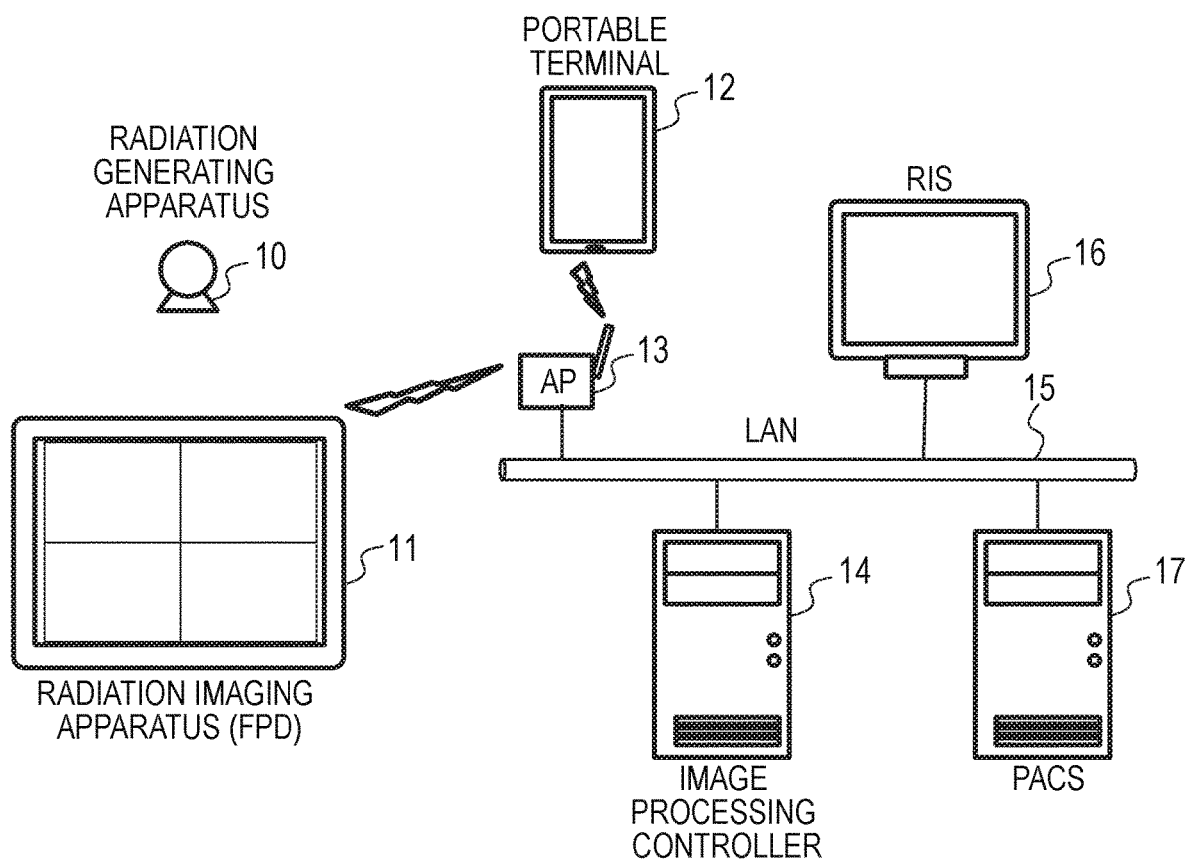
FIG. 1 is a configuration diagram illustrating an example of a radiation imaging system according to a first embodiment.
Figure 2:
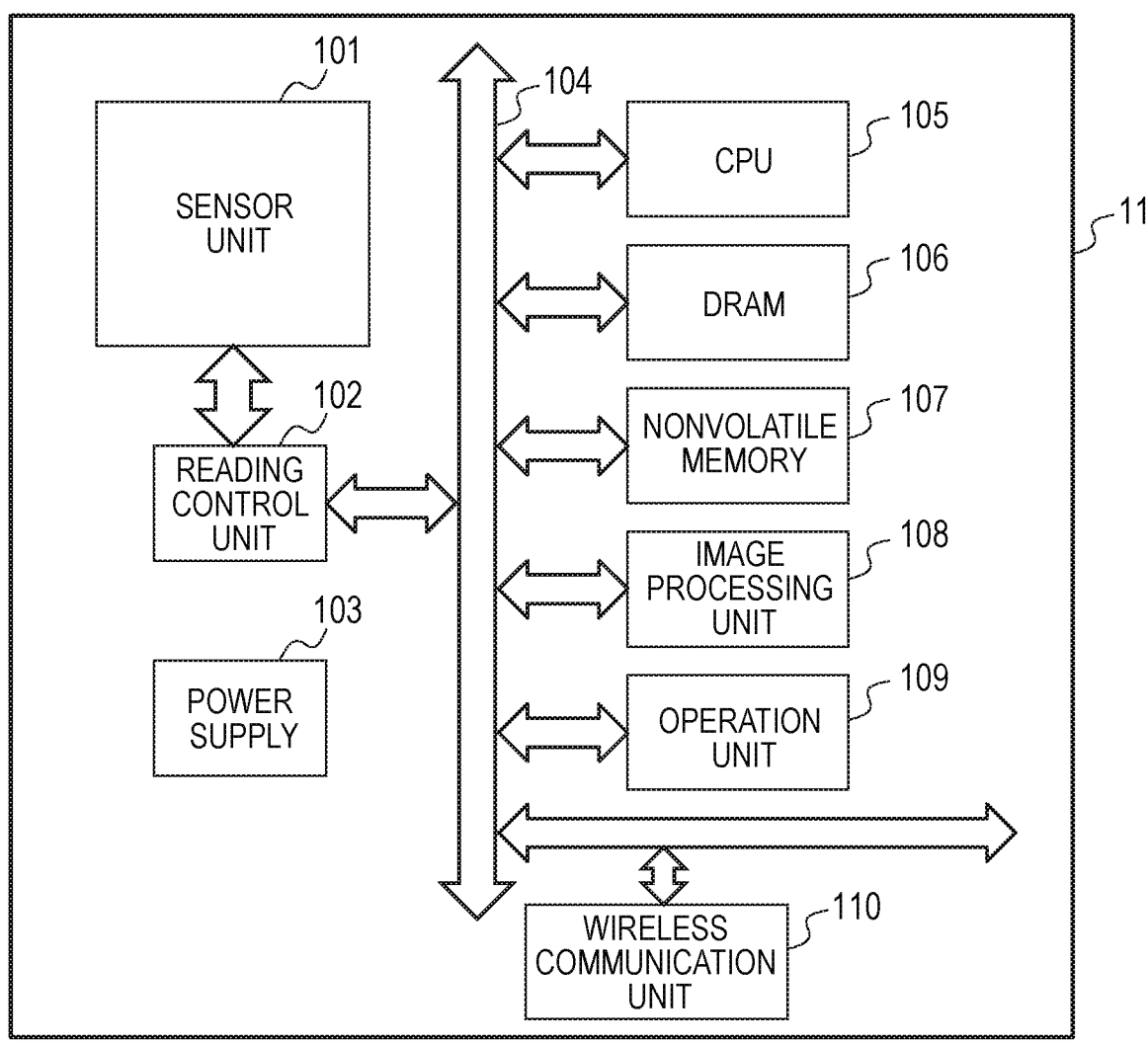
FIG. 2 is a block diagram illustrating an example of a radiation imaging apparatus according to the first embodiment.

FIG. 1 is a configuration diagram illustrating an example of a radiation imaging system according to a first embodiment in the present invention. A radiation imaging system according to the present embodiment is applicable to, for example, a medical image diagnosis apparatus, a nondestructive inspection apparatus, an analyzing apparatus using radiation, and the like. FIG. 2 is a block diagram illustrating an example of a radiation imaging apparatus (e.g., an FPD) according to the present embodiment.

As illustrated in FIG. 1, the radiation imaging system includes a radiation generating apparatus 10, a radiation imaging apparatus 11, a portable terminal (information terminal) 12, an access point 13 in a LAN line 15, an image processing controller (image processing unit) 14 that performs image processing on a radiation image, the LAN line 15, a radiology information system (RIS) 16 that manages medical examination information on a subject (including subject information), and a picture archiving and communication system (PACS) 17 that manages captured images.

The portable terminal 12 is capable of communicating with the radiation imaging apparatus 11 and image processing controller 14. The portable terminal 12 is capable of performing operations of various kinds of apparatuses relating to radiation imaging. In addition, the portable terminal 12 has a portability as a tablet terminal or a smartphone, but various kinds of information terminals other than the image processing controller 14 are available as the portable terminal 12 whether or not the information terminals have the portability. The LAN line 15 may be either wired or wireless.

In the medical radiation imaging system illustrated in FIG. 1, radiation exposed from the radiation generating apparatus 10 is detected by the radiation imaging apparatus 11 disposed at a position where the radiation passing through a body of a patient reaches. The radiation imaging apparatus 11 performs radiation imaging and generates radiation image data based on the detected radiation. The radiation imaging apparatus 11 generates a radiation image according to an amount of passing radiation and transmits the generated radiation image to the image processing controller 14 via the access point 13 and the LAN line 15.

The image processing controller 14 is capable of performing first image processing on the radiation image data to generate a first image and transmitting the first image to the portable terminal 12. By performing the first image processing on the radiation image data received from the radiation imaging apparatus 11, the image processing controller 14 converts the radiation image data to the first image, which has a high viewability, and transmits the first image to the portable terminal 12 via the LAN line 15 and the access point 13.

Receiving the radiation image subjected to the first image processing, the portable terminal 12 displays the radiation image on a screen. An operator can check the radiation image displayed on the portable terminal to determine success/failure of the radiation imaging. The operator operates the portable terminal 12 to determine the success/failure of the radiation imaging, and when the radiation imaging have succeeded, the operator proceeds to next radiation imaging.

According to the present embodiment, use of the portable terminal 12 dispenses with a need of equipping a medical trolley with a dedicated monitor, which reduces articles necessary in making rounds at sickrooms. In addition, rather than equipping the medical trolley with the image processing controller 14, disposing the image processing controller 14 as a high performance shared server connected to the LAN line 15 in a hospital enables further reduction of the articles necessary in making rounds at sickrooms.

In FIG. 2, the radiation imaging apparatus 11 includes a sensor unit 101, a reading control unit 102, a power supply 103, a bus 104, a CPU (processing unit) 105, a DRAM 106, a nonvolatile memory 107, an image processing unit 108, an operation unit 109, and a wireless communication unit 110. The radiation imaging apparatus 11 performs simple image processing (second image processing) on radiation image data to generate a second image and transmits the second image to the portable terminal 12.

The sensor unit 101 converts incident radiation to electric charge distribution information (radiation information). The reading control unit 102 converts electric charge distribution information accumulated in the sensor unit 101 to digital information and writes the digital information to the DRAM 106 and the like. The power supply 103 is a power source for the radiation imaging apparatus 11. The bus 104 connects blocks in the radiation imaging apparatus 11 together, implementing interactive communication of data. The CPU (processing unit) 105 controls the radiation imaging apparatus 11.

The DRAM 106 is used in accumulating the radiation image data and executing a program. The nonvolatile memory 107 such as a Flash ROM is used in storing code executed by the CPU 105 and the radiation image data. The image processing unit 108 subjects the radiation image read out from the sensor unit 101 to the DRAM 106 to the simple image processing (the second image processing). The operation unit 109 inputs operation information from the portable terminal 12. The wireless communication unit 110 transfers the radiation image and the radiation image subjected to the simple image processing to an external apparatus using a given communication method such as WiFi (registered trademark).

Figure 3:
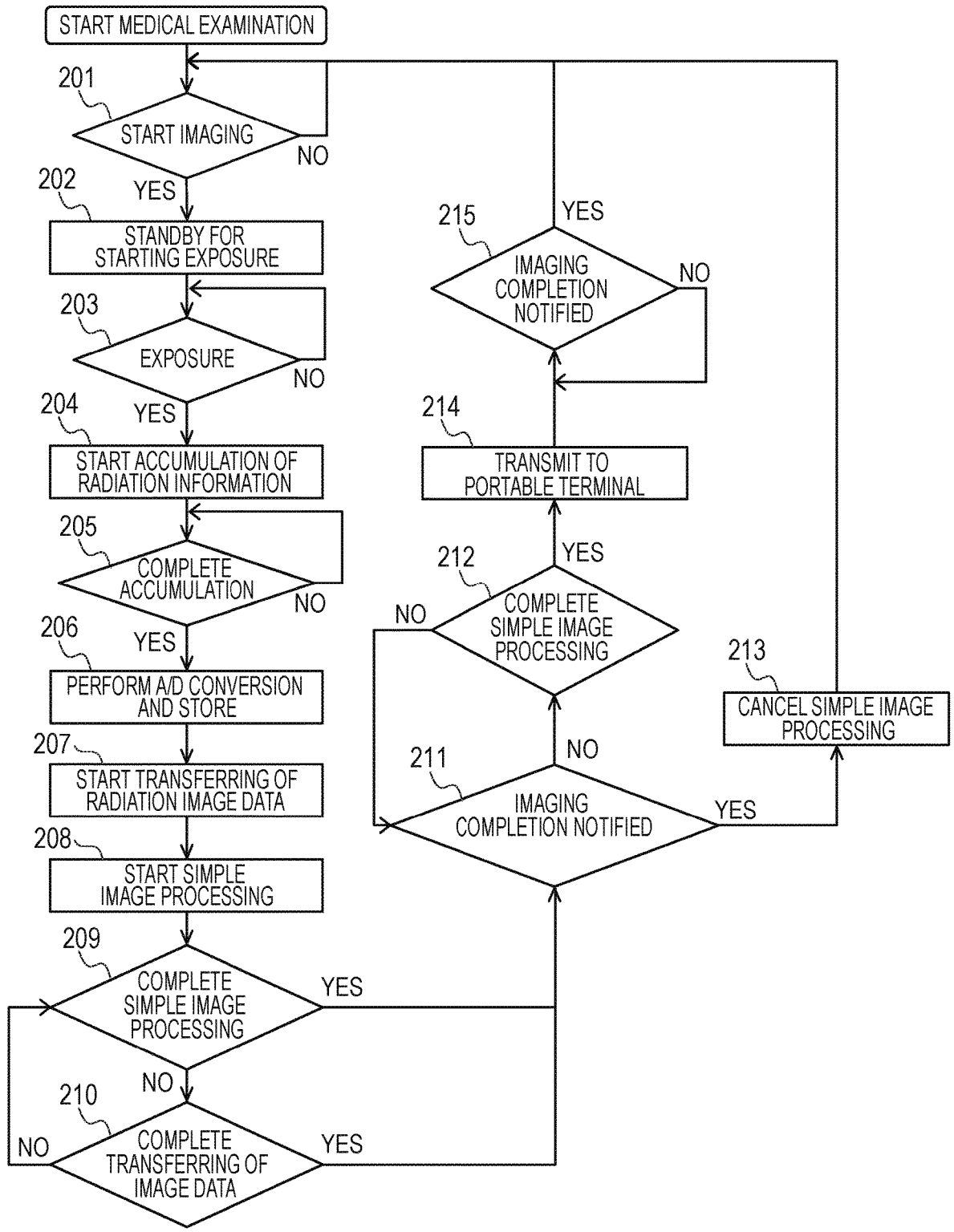
FIG. 3 is a flowchart illustrating operation of the radiation imaging apparatus in the first embodiment.
Figure 4:
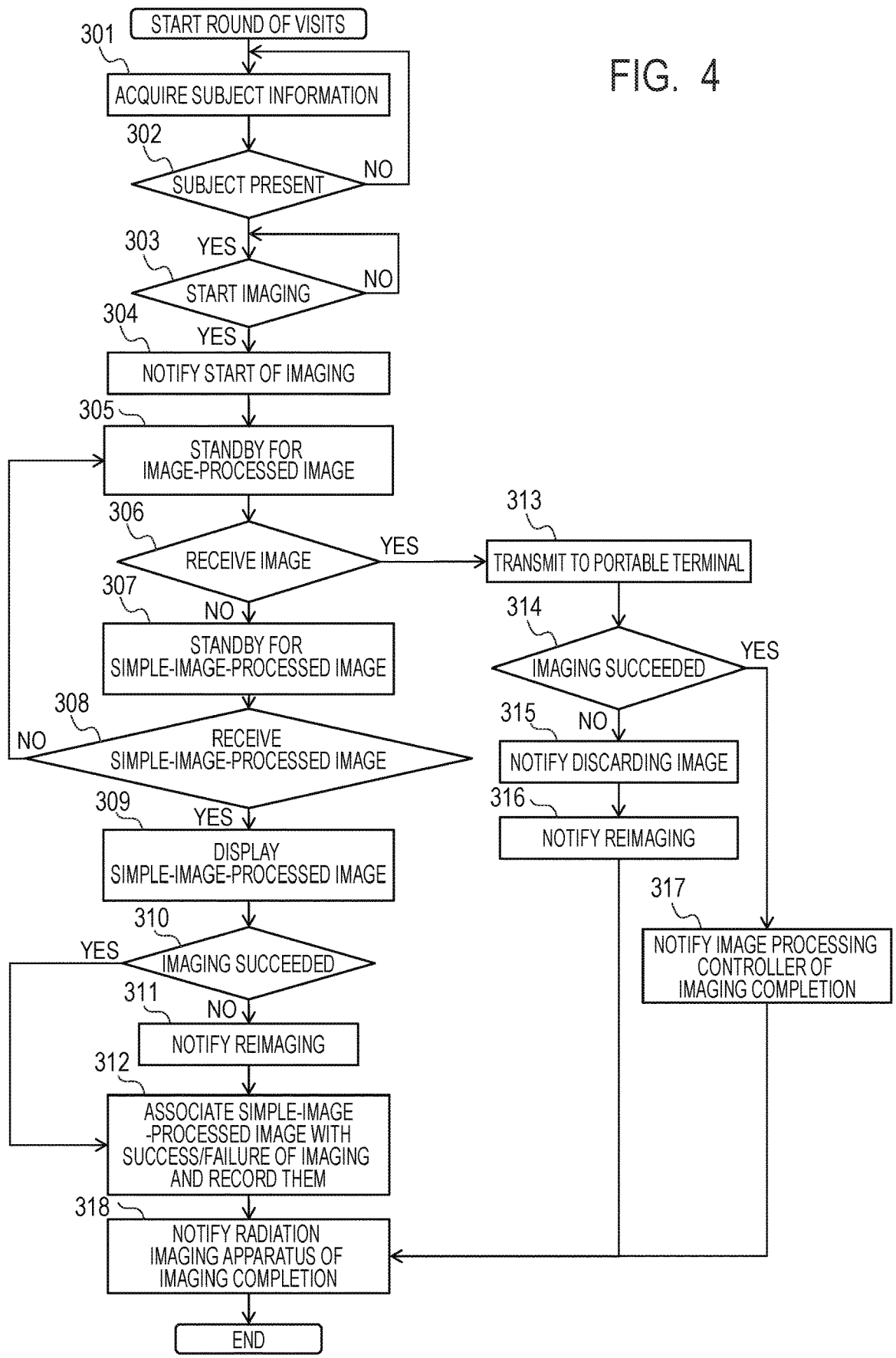
FIG. 4 is a flowchart illustrating operation of a portable terminal in the first embodiment.

FIG. 3 is a flowchart illustrating operation of the radiation imaging apparatus 11 in the present embodiment. FIG. 4 is a flowchart illustrating operation of the portable terminal 12 in the present embodiment.

The following description will be made on an assumption that the medical trolley is equipped with the radiation imaging system. Note that operation of the radiation imaging system according to the present invention is not limited to operation using the medical trolley.

In the radiation imaging system illustrated in FIG. 1, an operator operates the portable terminal 12 to acquire subject information on a subject to be subjected to radiation imaging, from the RIS 16 (step 301). It is determined whether the subject to be subjected to the imaging is present (step 302). When the subject is present, the operator drives the medical trolley to leave for a sickroom where the patient is waiting. At this time, the medical trolley is equipped with at least the radiation generating apparatus 10, the radiation imaging apparatus 11, and the portable terminal 12. In a case where the portable terminal 12 is a small portable terminal such as a smartphone, the operator can carry around the portable terminal 12.

Being prepared to perform the radiation imaging on the subject to be subjected to the imaging, the operator performs a starting operation of the radiation imaging with the portable terminal 12 (step 303). When the radiation imaging is started, the portable terminal 12 notifies the radiation imaging apparatus 11 of the start of the imaging (step 304).

Upon receiving the notification of the start of the imaging (step 201), the radiation imaging apparatus 11 proceeds to a standby state for starting exposure of radiation (step 202). Note that the standby for starting the exposure may be entered by the radiation imaging apparatus 11 being put on standby for receiving an electric trigger signal from the radiation generating apparatus 10. Alternatively, the standby for starting the exposure may be entered by the radiation imaging apparatus 11 being put on standby for automatic detection of irradiation with radiation by the radiation generating apparatus 10.

The operator operates the radiation generating apparatus 10 to exposure of radiation, performing radiation imaging.

In a case where the portable terminal 12 can be used to operate the radiation generating apparatus 10, the operator may operate the portable terminal 12 to perform the exposure of the radiation. Upon detecting the exposure of the radiation by the radiation generating apparatus 10 (step 203), the radiation imaging apparatus 11 starts to accumulate radiation information (step 204). The sensor unit 101 of the radiation imaging apparatus 11 accumulates the radiation in a form of electric charge distribution information.

When the accumulation of the electric charge distribution information is completed (step 205), the CPU 105 of the radiation imaging apparatus 11 outputs a command to the reading control unit 102. The reading control unit 102 performs A/D conversion on the electric charge distribution information accumulated in the sensor unit 101, writes the A/D converted electric charge distribution information to the DRAM 106 through the bus 104, and causes the DRAM 106 to store them (step 206). The digital data (electric charge distribution information) stored in the DRAM 106 is treated as radiation image data. The CPU 105 transfers the radiation image data to image processing controller 14 with the wireless communication unit 110, via the access point 13 and the LAN line 15 (step 207). The radiation image data is not limited to the digital data of the electric charge distribution information and may be a captured image generated from the data.

Before starting the transfer of the radiation image data to the image processing controller 14 (step 207), the CPU 105 or the image processing unit 108 may perform image preprocessing such as gain correction and defect pixel correction on the radiation image data.

In synchronization with the transfer of the radiation image data to the image processing controller 14 (step 207), the CPU 105 of the radiation imaging apparatus 11 transmits the radiation image data to the image processing unit 108 of the radiation imaging apparatus 11 to start the simple image processing (step 208). The simple image processing may be performed by the CPU 105 instead of the image processing unit 108.

After notifying the radiation imaging apparatus 11 of the start of the imaging (step 304), the portable terminal 12 proceeds to a standby state for receiving the radiation image subjected to the image processing by the image processing controller 14 (image-processed image) (step 305). After proceeding to the standby state for receiving the image from image processing controller 14 in step 305, the portable terminal 12 determines in step 306 whether the portable terminal 12 has received the image. In addition, the portable terminal 12 proceeds to a standby state for receiving the radiation image subjected to the simple image processing by the radiation imaging apparatus 11 (simple-image-processed image) (step 307). In FIG. 4, the process of step 306 is followed by the process of step 307, but note that the standby for and a reception determination process on the image in steps 305 and 306 and the standby for and a reception determination process on the image in steps 307 and 308 may be performed in parallel.

The image processing controller 14 subjects the radiation image data received from the radiation imaging apparatus 11 to advanced image processing including luminance optimization adjustment, edge enhancement, smoothing, contrast correction, and the like. In addition, after the advanced image processing, the image processing controller 14 transmits the image-processed image (first image) to the portable terminal 12 via the LAN line 15 and the access point 13.

In parallel to the image processing of the image processing controller 14, the radiation imaging apparatus 11 performs the simple image processing of step 208.

Here, in a case where a malfunction occurs in the access point 13 and the LAN line 15 forming a communication route or in the image processing controller 14, the transfer process from the radiation imaging apparatus 11 to the image processing controller 14 started in step 207 is disabled or delayed. It is assumed in this case that the simple image processing by the image processing unit 108 of the radiation imaging apparatus 11 is completed in step 209 before the transfer process from the radiation imaging apparatus 11 to the image processing controller 14 is completed in step 210.

In this case, the CPU 105 of the radiation imaging apparatus 11 checks for notification of completion of the imaging from the portable terminal 12 in step 318 (step 211). The portable terminal 12 notifies the radiation imaging apparatus 11 of the completion of the radiation imaging by inputting success/failure of the radiation imaging based on at least one of the first image from the image processing controller 14 and the second image from the radiation imaging apparatus 11.

If the transfer of the radiation image data from the radiation imaging apparatus 11 to the image processing controller 14 has not been completed, the image processing by the image processing controller 14 cannot be performed, and thus the completion of the radiation imaging is not notified in step 211. It is therefore assumed that the radiation imaging apparatus 11 cannot receive the completion of the radiation imaging in step 211 in a case where the simple image processing by the image processing unit 108 is completed before the transfer process to the image processing controller 14 has been completed. In a case where the radiation imaging has not been completed, the radiation imaging apparatus 11 confirms in step 212 that the simple image processing has been completed and then transmits the simple-image-processed image (second image) to the portable terminal 12 via the access point 13 (step 214).

In contrast, there is a case where the transfer process of the image data from the radiation imaging apparatus 11 to the image processing controller 14 is completed in step 210 before the simple image processing has been completed in step 209, and the case will be described. Also, in this case, the CPU 105 checks for the notification of the completion of the imaging from the portable terminal 12 in step 318 (step 211).

Although the transfer process from the radiation imaging apparatus 11 to the image processing controller 14 has been completed step 210, the image processing by the image processing controller 14 may be disabled or delayed. Additionally, in a case where a malfunction occurs in the communication route or the image processing controller 14, a transfer process of the image-processed image from the image processing controller 14 to the portable terminal 12 may be disabled or delayed. In these cases, it is assumed that the radiation imaging has not been completed in the portable terminal 12.

In a case where the radiation imaging apparatus 11 has not received the notification of the completion of the imaging in step 211, the radiation imaging apparatus 11 checks whether the simple image processing by the radiation imaging apparatus 11 has been completed (step 212). In a case where the simple image processing has been completed, the CPU 105 transmits the simple-image-processed image (second image) to the portable terminal 12 via the access point 13 (step 214).

As seen from the above, the radiation imaging apparatus 11 awaits the notification of the completion of the radiation imaging from the portable terminal 12, and after starting the transmission of the radiation image data to the image processing controller 14, the radiation imaging apparatus 11 transmits the second image to the portable terminal 12 in a case where the radiation imaging apparatus 11 has not received the notification of the completion of the imaging from the portable terminal 12.

In either of the above cases, the portable terminal 12 receives the simple-image-processed image from the radiation imaging apparatus 11 before receiving the image-processed image from the image processing controller 14 in step 306 (step 308). Accordingly, the portable terminal 12 displays the simple-image-processed image (second image) from the radiation imaging apparatus 11 (step 309), and the operator checks the second image displayed on the portable terminal 12 to determine the success/failure of the radiation imaging (step 310).

In a case where the portable terminal 12 inputs in step 310 the success of the radiation imaging based on the second image, the portable terminal 12 may perform instructions that cause the portable terminal 12 to transmit the second image to the PACS 17, or instructions that cause the radiation imaging apparatus 11 to transmit the second image to the PACS 17. Alternatively, in the case where the portable terminal 12 inputs the success of the radiation imaging based on the second image, the portable terminal 12 may perform instructions that cause the image processing controller 14 to transmit the first image to the PACS 17.

In a case where the portable terminal 12 inputs in step 310 the failure of the radiation imaging based on the second image (the radiation imaging has failed), reimaging is needed, and thus the portable terminal 12 notifies the radiation generating apparatus 10 as necessary that the radiation generating apparatus 10 is to perform the reimaging (step 311).

Thereafter, irrespective of the success/failure of the radiation imaging, the portable terminal 12 associates a fact about and a result of making the determination of the success/failure of the radiation imaging using the second image, with an information ID given to subject information or medical examination information and with the second image, and records them (step 312). This is for identifying a radiation image not subjected to the image processing by the image processing controller 14 later.

Subsequently to step 312, the portable terminal 12 notifies the radiation imaging apparatus 11 of the completion of the radiation imaging (step 318) and finishes the imaging.

In contrast, in a case where the image processing by the image processing controller 14 is completed without delay, the portable terminal 12 receives the image-processed image from the image processing controller 14 in step 306 before receiving the simple-image-processed image from the radiation imaging apparatus 11. In this case, the portable terminal 12 displays the image-processed image from the image processing controller 14 (step 313), and the operator checks the radiation image displayed on the portable terminal 12 to determine the success/failure of the radiation imaging (step 314).

In a case where it is determined in step 314 that the radiation imaging has failed, the portable terminal 12 notifies the image processing controller 14 that image processing controller 14 is to discard the image-processed image (first image) (step 315). As seen from the above, in the case where the portable terminal 12 inputs the failure of the radiation imaging based on the first image, the image processing controller 14 performs instructions to discard the first image.

In the case where it is determined in step 314 that the radiation imaging has failed, reimaging is needed, and thus the portable terminal 12 notifies the radiation generating apparatus 10 as necessary that the radiation generating apparatus 10 is to perform the reimaging (step 316). Subsequently to step 316, the portable terminal 12 notifies the radiation imaging apparatus 11 of the completion of the imaging (step 318) and finishes the imaging.

In a case where it is determined in step 314 that the radiation imaging has succeeded, the portable terminal 12 notifies the image processing controller 14 of the completion of the imaging (step 317). The image processing controller 14 then transmits the image-processed image by the image processing controller 14 to the PACS (image managing unit) 17.

As seen from the above, in the case where the portable terminal 12 inputs the success of the radiation imaging based on the first image (the radiation imaging has succeeded), the image processing controller 14 performs the instructions to transmit the first image to the PACS 17. In the case where the portable terminal 12 inputs the success of the radiation imaging based on the first image, the portable terminal 12 may perform the instructions to transmit the first image to the PACS.

Subsequently to step 317, the portable terminal 12 notifies the radiation imaging apparatus 11 of the completion of the radiation imaging (step 318) and finishes the imaging. Note that the portable terminal 12 may input the success/failure of the radiation imaging based on at least one of the first image and the second image at a time other than step 317 to notify the image processing controller 14 of the completion of the radiation imaging.

While the portable terminal 12 is in the standby state for the image-processed image (step 305 to step 308), the CPU 105 or the image processing unit 108 of the radiation imaging apparatus (FPD) 11 performs the simple image processing (step 208). In a case where the radiation imaging apparatus 11 receives the completion of the imaging from the portable terminal 12 (step 211, step 318) before the simple image processing is completed in step 209, the CPU 105 or the image processing unit 108 cancels the simple image processing (step 213) to prepare for the next imaging.

As seen from the above, in a case where the radiation imaging apparatus 11 receives the notification of the completion of the imaging from the portable terminal 12 after starting the transmission of the radiation image data to the image processing controller 14, the radiation imaging apparatus 11 cancels the second image processing. In this case, the radiation imaging apparatus 11 may discard the second image.

In contrast, in a case where the radiation imaging apparatus 11 does not receive the completion of the imaging from the portable terminal 12 (step 211, step 318) before the simple image processing is completed in step 209, the CPU 105 or the image processing unit 108 of the radiation imaging apparatus 11 continues the simple image processing.

In addition, in a case where the simple image processing has been completed (step 212) before the radiation imaging apparatus 11 receives the notification of the completion of the imaging from the portable terminal 12, the radiation imaging apparatus 11 transmits the simple-image-processed image to the portable terminal 12 (step 214). After the radiation imaging apparatus 11 transmits the simple-image-processed image to the portable terminal 12 (step 214), the CPU 105 of the radiation imaging apparatus 11 waits for the notification of the completion of the imaging from the portable terminal 12 (step 215), and upon receiving the notification of the completion of the imaging, the CPU 105 completes the imaging.

As seen from the above, the portable terminal 12 displays one of the first image and the second image received earlier. After the imaging of the radiation image (accumulation of the radiation information), one of the first image generated by the image processing controller 14 and the second image generated by the radiation imaging apparatus 11 reaching the portable terminal 12 earlier is displayed on the portable terminal 12, with which the success/failure of the radiation imaging is determined. The portable terminal 12 inputs the success/failure of the radiation imaging based on at least one of the first image and the second image.

Therefore, even in a case where the transfer process from the radiation imaging apparatus 11 to the image processing controller 14 is disabled or delayed due to a communication failure, a malfunction of an apparatus, or the like, the success/failure of the radiation imaging can be determined with the simple-image-processed image from the radiation imaging apparatus 11.

For example, when a communication failure occurs in the LAN line 15, the access point 13, or the like in a case where the image processing controller 14 transmits the first image to the portable terminal 12, the second image from the radiation imaging apparatus 11 can be used to determine the success/failure of the radiation imaging.

In a case where the portable terminal 12 receives the image-processed image (first image) by the image processing controller 14 from the image processing controller 14 before inputting the success/failure of the radiation imaging based on the simple-image-processed image (second image), the portable terminal 12 may display the first image.

The image processing performed by the image processing controller 14 and the simple image processing performed by the radiation imaging apparatus 11 have different levels of image processing. The reason for the difference in level of image processing is that the image processing controller 14 typically includes relatively high-performance hardware and software for image processing, whereas the radiation imaging apparatus 11 has resources for image processing poorer than those of the image processing controller 14. Accordingly, in the present embodiment, the simple image processing performed by the radiation imaging apparatus 11 is image processing that requires a light load for image processing as compared with the image processing performed by the image processing controller 14.

For example, assumable simple image processing includes performing the luminance optimization adjustment and the contrast correction but does not include some items of the image processing by the image processing controller 14, such as the edge enhancement and the smoothing. In addition, assumable simple image processing may be performed in such a manner that, for example, the image processing is performed but captured images are thinned out and contracted before the image processing. For example, the second image processing is performed on radiation image data of which a data amount is smaller than the radiation image data to be subjected to the first image processing.

Note that the simple image processing performed by the radiation imaging apparatus 11 may be the same image processing as the image processing performed by the image processing controller 14. In addition, the simple image processing performed by the radiation imaging apparatus 11 may be image processing of a higher level than that of the image processing performed by the image processing controller 14. In this case, the image processing performed by the image processing controller 14 has to take a time shorter than a time taken by the image processing performed by the radiation imaging apparatus 11.

In such a manner, the time taken by the second image processing can be made shorter than the time taken by the first image processing. For example, processing steps of the second image processing can be made fewer than processing steps of the first image processing.

Next, the information ID used in step 312 will be described. An example of operation of the radiation imaging system according to the present embodiment is to use a medical trolley. Assume a case where a medical trolley performs the radiation imaging in making rounds at a plurality of sickrooms and thereafter returns to a standby place of the medical trolley. In this case, radiation images captured while the medical trolley makes a round of visits include radiation image of which success/failure is checked using image-processed images processed by the image processing controller 14 and radiation images of which success/failure is checked using simple-image-processed images processed by the radiation imaging apparatus 11 in a mixed manner.

When the medical trolley returns to the standby place, the operator operates the portable terminal 12 to display the image-processed images processed by the image processing controller 14 during making the round of visits of the medical trolley on the portable terminal 12 and checks for a success/failure of a radiation image for which a success/failure of imaging cannot be checked during the round of visits of the medical trolley. In addition, there is a case where a success/failure of imaging is not checked using an image-processed image processed by the image processing controller 14 during normal imaging.

Figure 5:
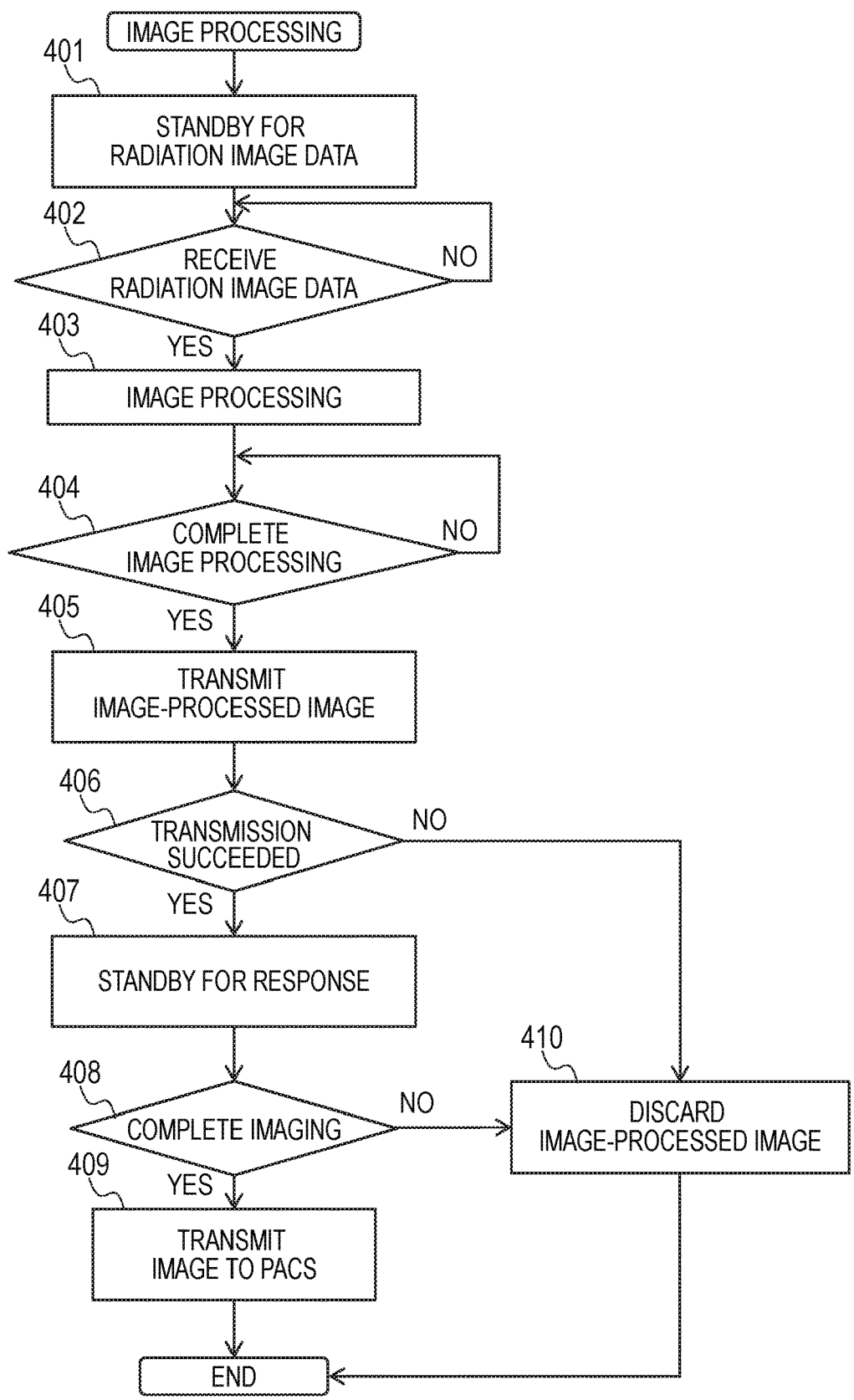
FIG. 5 is a flowchart illustrating operation of an image processing controller in the first embodiment.

FIG. 5 is a flowchart illustrating operation of the image processing controller 14. As illustrated in FIG. 5, the image processing controller 14 steadily awaits a captured image (radiation image data) by the radiation imaging apparatus 11 (step 401). The radiation image data transmitted from the radiation imaging apparatus 11 is given an information ID for identifying subject information or medical examination information and given a terminal ID for identifying a portable terminal 12 that has requested the radiation imaging apparatus 11 to capture the radiation image.

When the radiation image data including the given information is transmitted from the radiation imaging apparatus 11 to the image processing controller 14, the image processing controller 14 subjects the received radiation image data to the image processing (step 402, step 403). When the image processing is completed (step 404), the image processing controller 14 uses the terminal ID to transmit the image-processed image to the portable terminal 12 that has requested the radiation imaging apparatus 11 to capture the image (step 405).

In a case where the transmission of the image-processed image to the portable terminal 12 has failed due to a communication failure, a malfunction of an apparatus, or the like (step 406), the image processing controller 14 discards the image-processed image (step 410) and finishes the image processing on the radiation image data in question.

In contrast, in a case where the transmission of the image-processed image to the portable terminal 12 has succeeded (step 406), the image processing controller 14 is put on standby for a response from the portable terminal 12, which is a transmission destination of the image-processed image (step 407). When the portable terminal 12 notifies the image processing controller 14 of the completion of the imaging in step 317, the image processing controller 14 receives the notification of the completion of the imaging, which is the response from the portable terminal 12 (step 408). In this case, the image processing controller 14 recognizes that the image-processed image by the image processing controller 14 has been confirmed as available in diagnosis (the success of the imaging), and the image processing controller 14 transmits the image-processed image to the PACS 17 (step 409). The PACS 17 stores the image-processed image.

In contrast, in a case where, in step 408, the image processing controller 14 does not receive the notification of the completion of the imaging from the portable terminal 12 or receives the notification of discarding the image in step 315, the image processing controller 14 discard the first image (step 410) and finishes the first image processing.

Figure 6:
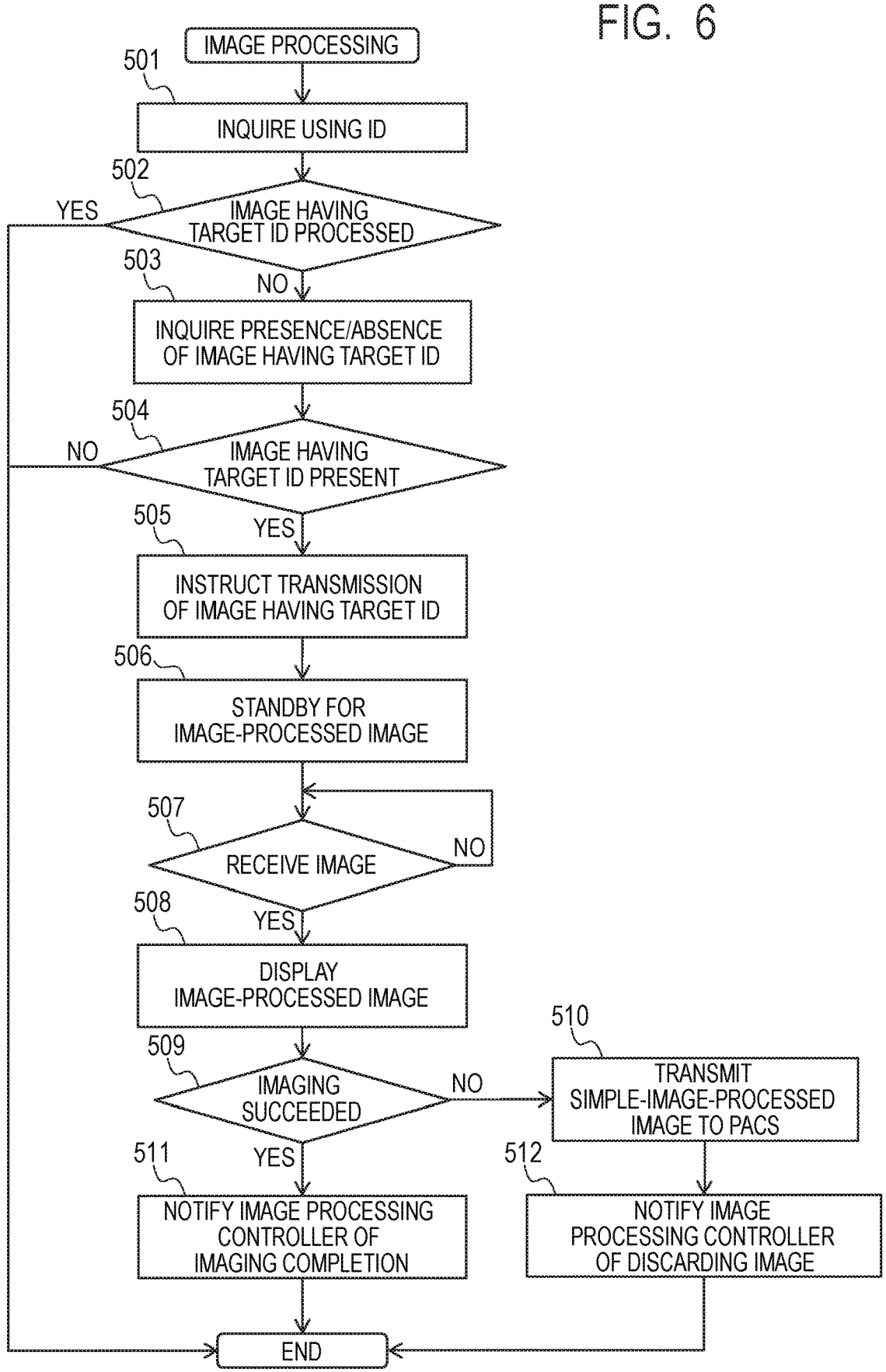
FIG. 6 is a flowchart illustrating an example of a process in which the portable terminal in the first embodiment checks an image-processed image.

FIG. 6 is a flowchart illustrating an example of a process in which the portable terminal 12 checks an image-processed image in a case where the portable terminal 12 does not use the image-processed image processed by the image processing controller 14 to check whether imaging has succeeded or failed.

In this case, the portable terminal 12 acquires image information on the simple-image-processed image, such as the simple-image-processed image and an icon or a thumbnail associated with the simple-image-processed image (hereinafter, referred to as "simple check information"). An image ID (related information) corresponding to the simple check information associates radiation image data before subjected to the simple image processing by the radiation imaging apparatus 11, the simple-image-processed image processed by the radiation imaging apparatus 11, and the image-processed image processed by the image processing controller 14.

When the operator causes the portable terminal 12 to select the simple check information, the portable terminal 12 inquires of the image processing controller 14 whether the process on a radiation image corresponding to the simple check information has been completed, based on the image ID (step 501). As seen from the above, in the case where the portable terminal 12 does not input the success/failure of the radiation imaging based on the first image, the portable terminal 12 checks whether the first image has been generated by the image processing controller 14.

In FIG. 6, the inquiry about whether the image processing has been completed in step 501 is made to the image processing controller 14 but may be made to a modality performed procedure step (MPPS). This allows a status of a medical examination to be known.

In a case where a result of the inquiry in step 501 shows that the image processing on the corresponding image ID has been completed in step 502, the portable terminal 12 finishes an image checking process. In this case, the image processing controller 14 performs the image processing on the radiation image and transmits the image-processed image to the PACS 17.

In contrast, in a case where the first image processing has not been completed in step 502 (including a case where the corresponding image ID has not been recorded), the portable terminal 12 inquire whether radiation image data of the corresponding image ID is saved in the radiation imaging apparatus 11 (step 503). The radiation image data on the captured image is radiation image data before subjected to the simple image processing. As seen from the above, in a case where the first image has not been generated by the image processing controller 14, the portable terminal 12 checks whether the radiation image data is stored in the radiation imaging apparatus 11.

In a case where the radiation image data corresponding to the image ID is not present in the radiation imaging apparatus 11 in step 504, the portable terminal 12 finishes the image checking process. In contrast, in a case where the radiation image data corresponding to the image ID is present in the radiation imaging apparatus 11 in step 504, the portable terminal 12 instructs the radiation imaging apparatus 11 to transmit the radiation image data on the captured image to the image processing controller 14 (step 505). In such a manner, in the case where the radiation image data is stored in the radiation imaging apparatus 11, the portable terminal 12 instructs the radiation imaging apparatus 11 to transmit the radiation image data to the image processing controller 14.

The radiation imaging apparatus 11 receives the instructions given in step 505 and transmits the radiation image data corresponding to the image ID to the image processing controller 14. The image processing controller 14 starts a series of processes in the image processing illustrated in FIG. 5, and when the image processing is completed, the image processing controller 14 transmits an image-processed image to the portable terminal 12 (step 405). After transmitting the instructions to the radiation imaging apparatus 11 in step 505, the portable terminal 12 is put on standby for receiving the image-processed image from the image processing controller 14 (step 506).

In step 507, in a case where the portable terminal 12 receives the image-processed image, the portable terminal 12 displays the image subjected to the image processing by the image processing controller 14, and the operator determines a success/failure of the radiation imaging (step 509).

In a case where the operator determines in step 509 that the captured image is available in diagnosis (the radiation imaging has succeeded), the portable terminal 12 notifies the image processing controller 14 of the completion of the imaging (step 511). The image processing controller 14 receives the notification of the completion of the imaging and transmits the image-processed image to the PACS 17 and causes the PACS 17 to store the image-processed image, as described above (step 409).

In contrast, in a case where the operator determines in step 509 that the captured image is unavailable in diagnosis (the radiation imaging has failed), the portable terminal 12 transmits a simple-image-processed image stored in the portable terminal 12 to the PACS 17 based on the image ID (step 510). In a case where the portable terminal 12 inputs the failure of the radiation imaging based on the first image, the portable terminal 12 may perform instructions to transmit the second image to the PACS 17, or the radiation imaging apparatus 11 may perform the instructions to transmit the second image to the PACS 17.

In addition, the portable terminal 12 notifies the image processing controller 14 of discarding the image corresponding to the image ID (step 512). The checking process may be finished without the process of step 512. Also, in this case, the image processing controller 14 discards the image-processed image in step 410 as described above and finishes the image processing on the radiation image data.

Second Embodiment

A second embodiment of the present invention will be described with reference to the drawings. Configurations, functions, and operations that are the same as those in the above embodiment will not be described, and differences of the present embodiment from the above embodiment will be mainly described.

Figure 7:
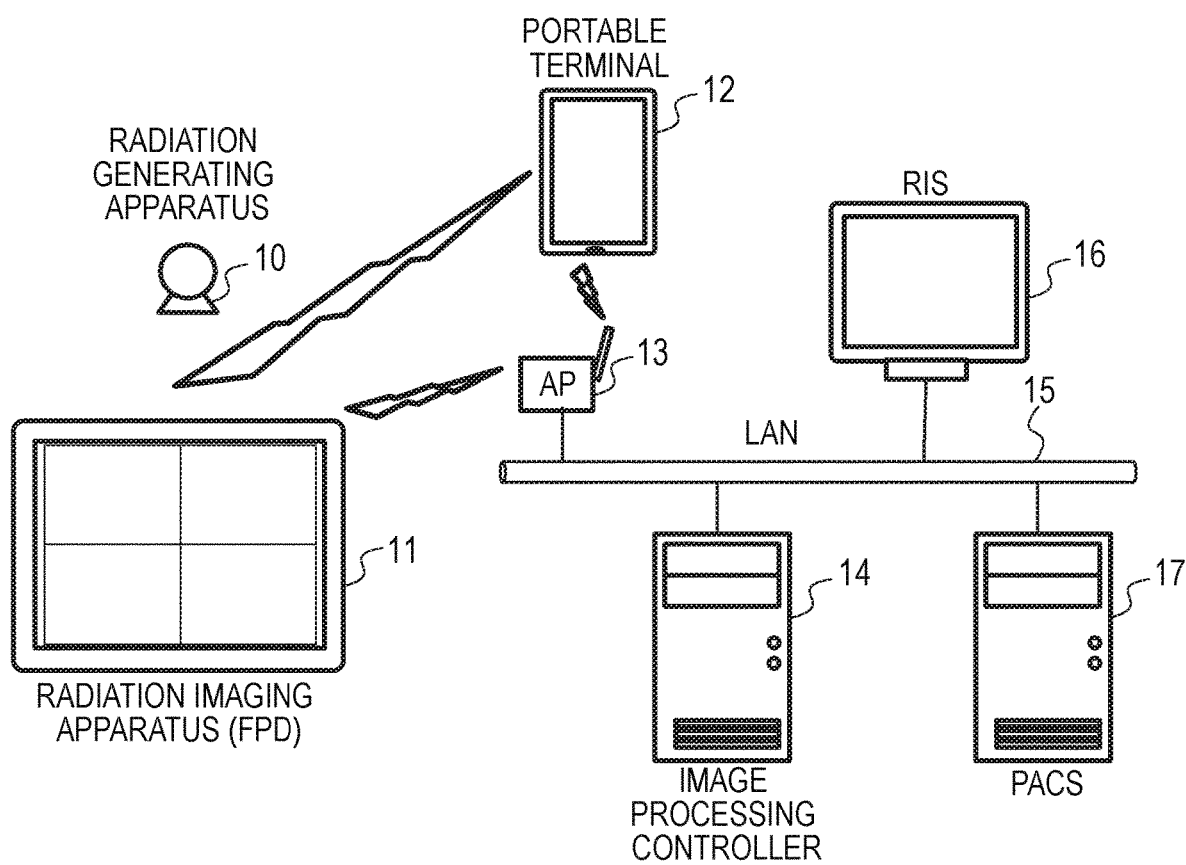
FIG. 7 is a diagram illustrating an example of a configuration according to a second embodiment.
Figure 8:
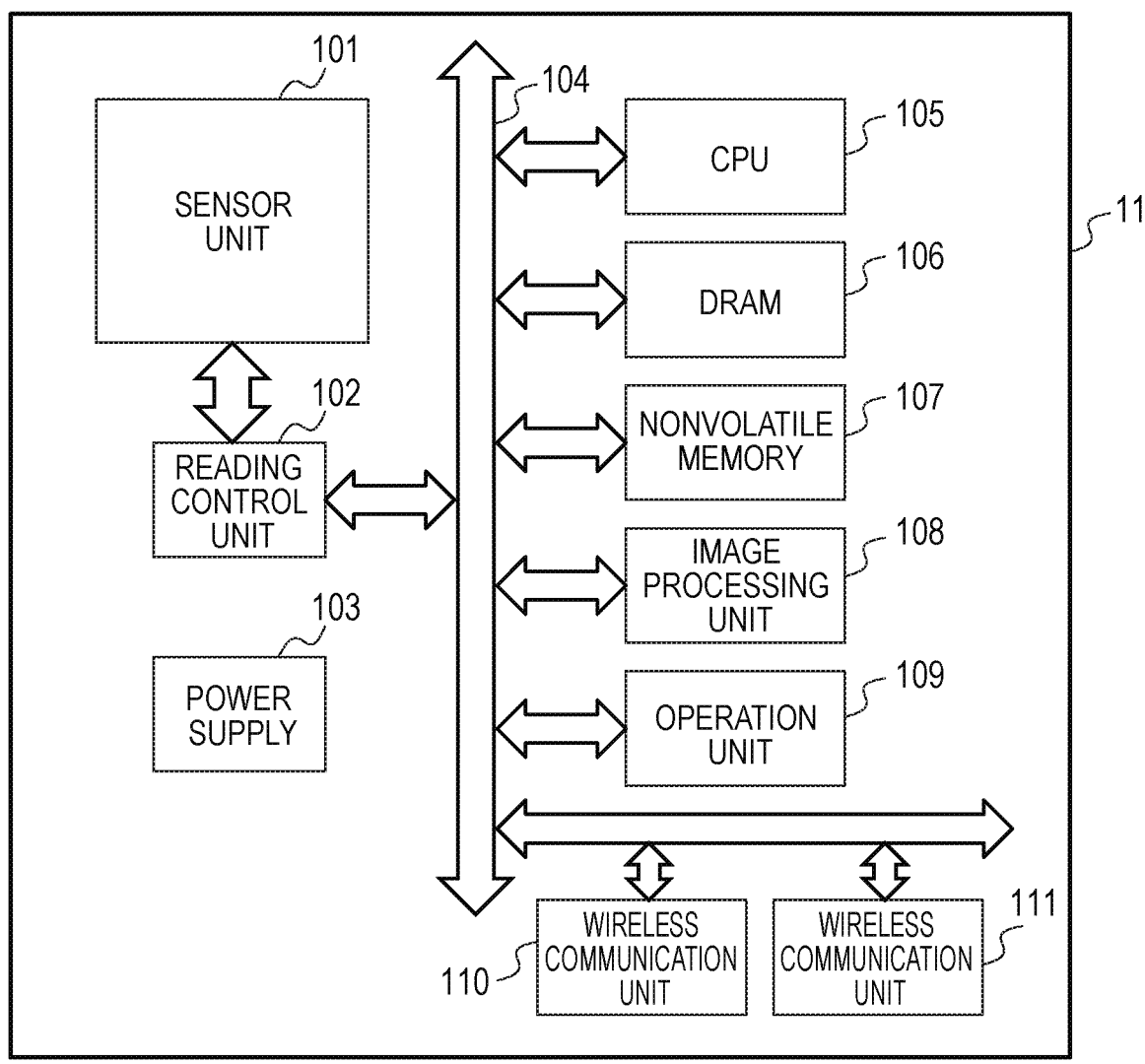
FIG. 8 is a block diagram illustrating an example of a radiation imaging apparatus in the second embodiment.

FIG. 7 is a diagram illustrating an example of a configuration according to the present embodiment. As illustrated in FIG. 7, a difference from the first embodiment is in that, in addition to a communication unit between a radiation imaging apparatus 11 and the access point 13 (first communication unit), a communication unit between the radiation imaging apparatus 11 and the portable terminal 12 (second communication unit) is provided. FIG. 8 is a block diagram of an example of the radiation imaging apparatus 11 according to the present embodiment. As illustrated in FIG. 8, a difference from the first embodiment is in that, in addition to the wireless communication unit (a first communication unit) 110, a wireless communication unit (a second communication unit) 111 is provided to support the new communication unit.

Operations of constituting units in the present embodiment are basically the same as the operations of constituting units in the first embodiment, but there is a difference in that the second communication unit using the second wireless communication unit 111 is used as the communication unit between the radiation imaging apparatus 11 and the portable terminal 12. The second communication unit may be a wireless communication unit using any communication technique including Bluetooth (registered trademark) and the like or may be a wired communication unit.

The portable terminal 12 is capable of receiving the first image from the image processing controller 14 via the first communication unit and capable of receiving the second image from the radiation imaging apparatus 11 via the second communication unit.

As seen from the above, the radiation imaging apparatus 11 transits a simple-image-processed image to the portable terminal 12 using the second communication unit, which is different from the first communication unit being a normal communication unit. This enables a simple-image-processed image to be transmitted from the radiation imaging apparatus 11 to the portable terminal 12 even in a case where a problem arises in the first communication unit between the radiation imaging apparatus 11 and the image processing controller 14 or between the portable terminal 12 and the image processing controller 14. As a result, even in a case communication using the first communication unit is disabled or delayed by a predetermined time period or longer, a success/failure of radiation imaging can be determined with the portable terminal 12.

The portable terminal 12 is capable of receiving the second image from the radiation imaging apparatus 11 via the first communication unit. In the case where the communication using the first communication unit is disabled or delayed by the predetermined time period or longer, the portable terminal 12 may switch from the first communication unit to the second communication unit to be able to receive a second image from the radiation imaging apparatus 11 via the second communication unit.

In addition, in a case where a problem arises in the first communication unit, the portable terminal 12 may detect the problem in the first communication unit and use the second communication unit to give instructions to switch a wireless channel using the first communication unit. The portable terminal 12 is capable of receiving a second image from the radiation imaging apparatus 11 via the first communication unit, and in the case where the communication using the first communication unit is disabled or delayed by the predeter-mined time period or longer, the portable terminal 12 can use the second communication unit to rebuild a network using the first communication unit.

With the switching instructions using the second communication unit, the portable terminal 12 can instruct the radiation imaging apparatus 11 to rebuild a network using the switched wireless channel.

In this case, with the first communication unit, the radiation imaging apparatus 11 and the portable terminal 12 can rebuild the network and communicate a simple-image-processed image. For example, in a case where a transmission speed of the first communication unit is higher than a transmission speed of the second communication unit, it is possible to transmit instructions to switch the wireless channel using the second communication unit and transmit a radiation image to the portable terminal 12 using the first communication unit to which the wireless channel is switched, which enables the transmission to be processed at high-speed. Alternatively, the network using the first communication unit may be rebuilt by resetting apparatuses implementing the first communication unit.

In a case where the second communication unit slower than the first communication unit is used, a required time of the transmission can be reduced by transmitting a simple-image-processed image from the radiation imaging apparatus 11 to the portable terminal 12.

Assumable simple image processing includes performing the luminance optimization adjustment and the contrast correction but does not include some items of the image processing by the image processing controller 14, such as the edge enhancement and the smoothing. In addition, assumable simple image processing may be performed in such a manner that, for example, the image processing is performed but captured images are thinned out and contracted before the image processing. For example, the second image processing is performed on radiation image data of which a data amount is smaller than the radiation image data to be subjected to the first image processing.

Third Embodiment

A third embodiment of the present invention will be described with reference to the drawings. Configurations, functions, and operations that are the same as those in the above embodiment will not be described, and differences of the present embodiment from the above embodiment will be mainly described.

In the present embodiment, the radiation imaging apparatus 11 transmits radiation image data to the portable terminal 12, and the portable terminal 12 subjects the radiation image data to the simple image processing (second image processing) to generate a simple-image-processed image (second image).

Figure 9:
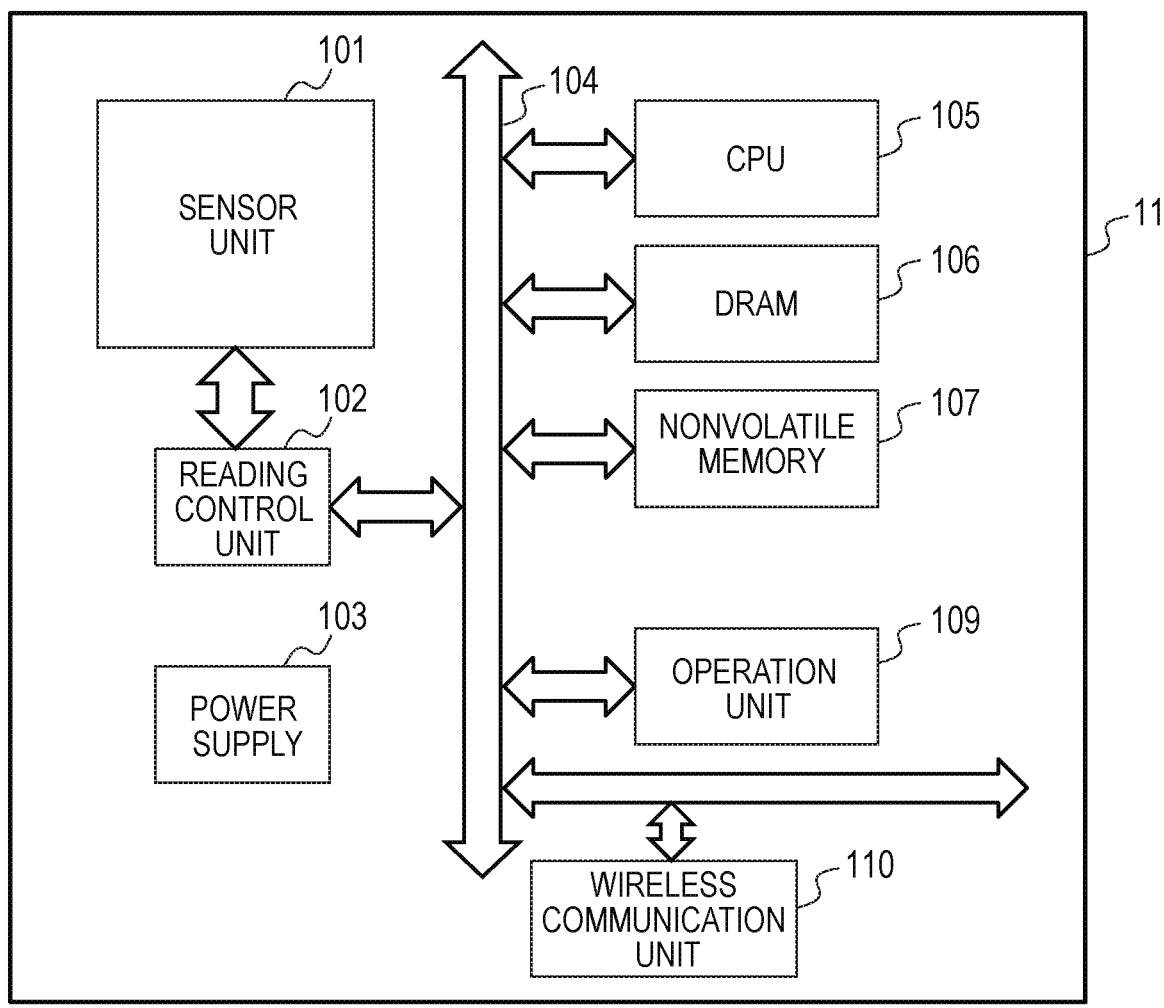
FIG. 9 is a block diagram illustrating an example of a radiation imaging apparatus in a third embodiment.
Figure 10:
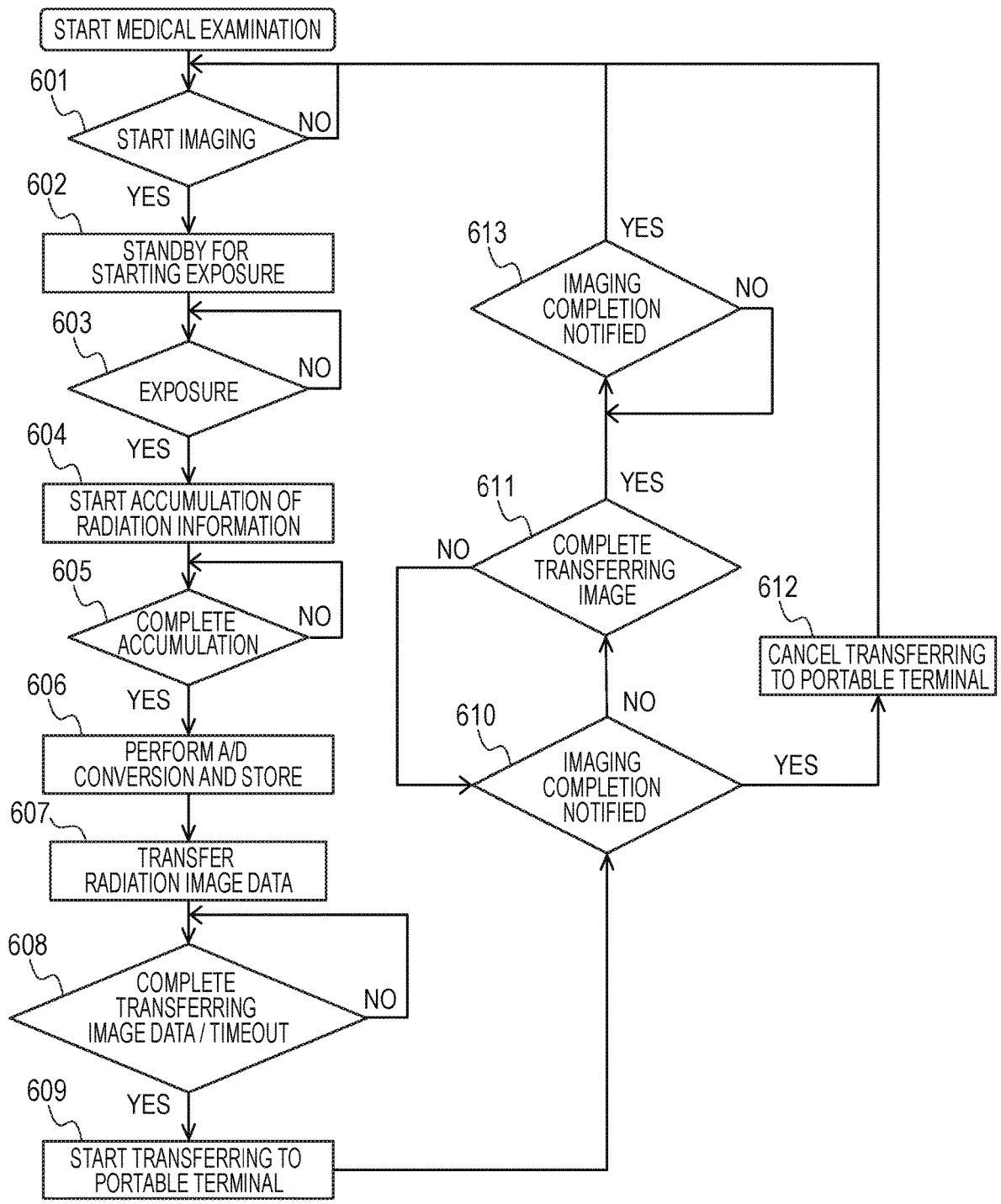
FIG. 10 is a flowchart illustrating operation of the radiation imaging apparatus in the third embodiment.

FIG. 9 is a block diagram illustrating an example of a radiation imaging apparatus 11 according to the present embodiment. A configuration diagram of a radiation imaging system according to the present embodiment is the same as FIG. 1. As illustrated in FIG. 9, in the present embodiment, as compared with other embodiments, the image processing unit 108 of the radiation imaging apparatus 11 is eliminated, and the simple image processing is performed by the portable terminal 12. FIG. 10 is a flowchart illustrating operation of the radiation imaging apparatus 11 according to the present embodiment. FIG. 11 is a flowchart illustrating operation of the portable terminal 12 in the present embodiment. Note that operations of constituting units other than the radiation imaging apparatus 11 and the portable terminal 12 in the present embodiment are the same as operations of constituting units in other embodiments.

In the radiation imaging system, the portable terminal 12 is caused to acquire subject information from the RIS 16 by an operator (step 701), and through step 702 and step 703, the portable terminal 12 notifies the radiation imaging apparatus 11 of starting imaging (step 704). Operations of the portable terminal 12 from step 701 to step 704 are the same as those in the first embodiment.

Meanwhile, the radiation imaging apparatus 11 receives the notification of the start of imaging from the portable terminal 12 (step 601), and through step 602 to step 606, starts transmitting radiation image data on a captured image to the image processing controller 14 (step 607). Processes of step 601 to step 607 are the same as those in the first embodiment.

In step 608 after step 607, in a case where the transmission of the radiation image data to the image processing controller 14 has been completed, the radiation imaging apparatus 11 starts transferring the radiation image data to the portable terminal 12 (step 609). Even in a case where the transfer of the radiation image data from the radiation imaging apparatus 11 to the image processing controller 14 is not completed within a predetermined time period in step 608, the radiation imaging apparatus 11 may perform timeout processing to proceed to step 609.

The reason for giving a higher priority the transfer of the image data to the image processing controller 14 in step 607 and step 608 than the transfer of the image data to the portable terminal 12 in step 609 is not to slow a response through a normal processing path.

In a case where the radiation imaging apparatus 11 receive a notification of completion of the radiation image from the portable terminal 12 (step 610) before transmission of the radiation image data to the portable terminal 12 has been completed in step 611, the radiation imaging apparatus 11 cancels the transmission of the radiation image data to the portable terminal 12 (step 612).

The portable terminal 12 awaits the start of the transfer of the radiation image data from the radiation imaging apparatus 11 in step 609 (step 705). Until receiving the radiation image data from the radiation imaging apparatus 11 in step 706, the portable terminal 12 awaits the radiation image data from the radiation imaging apparatus 11. In addition, the portable terminal 12 awaits an image-processed image from the image processing controller 14 (step 708, step 710).

In a case where the portable terminal 12 receives the radiation image data from the radiation imaging apparatus 11 earlier than the image-processed image from the image processing controller 14 in step 706, the portable terminal 12 starts the simple image processing on the radiation image data received from radiation imaging apparatus 11 (step 707). After starting the simple image processing, the portable terminal 12 awaits the image-processed image from the image processing controller 14 until the simple image processing is completed in step 709 (step 711, step 712).

In contrast, in a case where the portable terminal 12 receives the image-processed image from the image processing controller 14 earlier than the radiation image data from the radiation imaging apparatus 11 in step 710, the portable terminal 12 displays the image-processed image received from the image processing controller 14 (step 714).

In addition, in a case where the portable terminal 12 receives the image-processed image from the image processing controller 14 earlier than completion of the image processing by the portable terminal 12 in step 712, the portable terminal 12 displays the image-processed image received from the image processing controller 14 (step 714).

In contrast, in a case where the portable terminal 12 completes the image processing earlier than receiving the image-processed image from the image processing controller 14 in step 709, the portable terminal 12 displays a simple-image-processed image processed by the portable terminal 12 (step 713).

Operations of the portable terminal 12 in step 713, step 714, and steps subsequent to step 714 are substantially the same as those in the first embodiment. The portable terminal 12 however records a fact about and a result of making determination of a success/failure of the radiation imaging using the simple-image-processed image processed by the portable terminal 12, together with an information ID given to subject information and medical examination information, and the simple-image-processed image (step 720). The portable terminal 12 then notifies the radiation imaging apparatus 11 of the completion of the imaging (step 722).

As an application example and a range of application in the present embodiment, conditions described in the first embodiment and the second embodiment are applicable.

As in the second embodiment, in a case of where the second communication unit slower than the first communication unit is used, a required time of transmission can be reduced by transmitting radiation image data that is thinned out and contracted from the radiation imaging apparatus 11 to the portable terminal 12 in step 609. The second image processing is performed on radiation image data of which a data amount is smaller than the radiation image data to be subjected to the first image processing.

According to the above embodiments, by generating a second image and transmitting the second image to an information terminal, a radiation imaging unit can check a success/failure of radiation imaging even in a case where transmission of a first image from an image processing unit to the information terminal is disabled or delayed.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging system, comprising:
a radiation imaging unit configured to perform radiation imaging and generate radiation image data based on detected radiation; and
an image processing unit configured to perform first image processing on the radiation image data to generate a first image and capable of transmitting the first image to an information terminal, wherein
the radiation imaging unit is configured to subject the radiation image data to second image processing to generate a second image and transmit the second image to the information terminal; and
wherein the radiation imaging unit is configured to:
await a notification of completion of the radiation imaging from the information terminal; and
transmit the second image to the information terminal in a case where the radiation imaging unit does not receive the notification from the information terminal after starting transmission of the radiation image data to the image processing unit.

2. The radiation imaging system according to claim 1, wherein the information terminal is configured to display one of the first image and the second image received earlier.

3. The radiation imaging system according to claim 1, wherein the radiation imaging unit is configured to perform at least one of cancelling the second image processing and discarding the second image in a case where the radiation imaging unit receives the notification from the information terminal after starting the transmission of the radiation image data to the image processing unit.

4. The radiation imaging system according to claim 1, wherein the information terminal is configured to display the first image in a case where the information terminal receives the first image from the image processing unit before inputting a success/failure of the radiation imaging based on the second image.

5. The radiation imaging system according to claim 1, wherein the information terminal is configured to notify at least one of the radiation imaging unit and the image processing unit of completion of the radiation imaging by inputting a success/failure of the radiation imaging based on at least one of the first image and the second image.

6. The radiation imaging system according to claim 1, wherein
the information terminal is configured to:
check whether the first image is generated by the image processing unit in a case where the information terminal does not input a success/failure of the radiation imaging based on the first image;
check whether the radiation image data is stored in the radiation imaging unit in a case where the first image is not generated by the image processing unit; and
instruct the radiation imaging unit to transmit the radiation image data to the image processing unit in a case where the radiation image data is stored in the radiation imaging unit.

7. The radiation imaging system according to claim 1, wherein the information terminal is configured to:
input a success/failure of the radiation imaging based on at least one of the first image and the second image;
perform at least one of an instruction causing the information terminal to transmit the first image to an image managing unit and an instruction causing the image processing unit to transmit the first image to the image managing unit in a case where the information terminal inputs a success of the radiation imaging based on the first image; and
perform at least one of an instruction causing the information terminal to transmit the second image to the image managing unit, an instruction causing the radiation imaging unit to transmit the second image to the image managing unit, and an instruction causing the image processing unit to transmit the first image to the image managing unit in a case where the information terminal inputs a success of the radiation imaging based on the second image.

8. The radiation imaging system according to claim 1, wherein
the information terminal is configured to:
input a success/failure of the radiation imaging based on the first image; and
perform at least one of an instruction causing the information terminal to transmit the second image to an image managing unit, an instruction causing the radiation imaging unit to transmit the second image to the image managing unit, and an instruction causing the image processing unit to discard the first image in a case where the information terminal inputs a failure of the radiation imaging based on the first image.

9. The radiation imaging system according to claim 1, wherein
the information terminal is:
capable of receiving the first image from the image processing unit via a first communication unit; and
capable of receiving the second image from the radiation imaging unit via a second communication unit.

10. The radiation imaging system according to claim 9, wherein
the information terminal is:
capable of receiving the second image from the radiation imaging unit via the first communication unit; and
capable of switching from the first communication unit to the second communication unit to receive the second image from the radiation imaging unit via the second communication unit.

11. The radiation imaging system according to claim 9, wherein
the information terminal is:
capable of receiving the second image from the radiation imaging unit via the first communication unit; and
configured to rebuild a network of the of the first communication unit using the second communication unit.

12. The radiation imaging system according to claim 1, wherein a processing time period of the second image processing is shorter than a processing time period of the first image processing.

13. The radiation imaging system according to claim 1, wherein processing steps of the second image processing are fewer than processing steps of the first image processing.

14. The radiation imaging system according to claim 1, wherein the second image processing is performed on the radiation image data of which a data amount is smaller than the radiation image data to be subjected to the first image processing.

15. A radiation imaging method comprising:
performing, by a radiation imaging unit, radiation imaging and generating radiation image data based on detected radiation;
performing, by an image processing unit, first image processing on the radiation image data to generate a first image and transmitting the first image to an information terminal;
subjecting, by the radiation imaging unit, the radiation image data to second image processing to generate a second image;
awaiting, by the radiation imaging unit, a notification of completion of the radiation imaging from the information terminal; and
transmitting, by the radiation imaging unit, the second image to the information terminal in a case where the radiation imaging unit does not receive the notification from the information terminal after starting transmission of the radiation image data to the image processing unit.

16. A non-transitory computer-readable storage medium storing a program for causing a processor to perform a radiation imaging method when the program is executed by the processor, the radiation imaging method comprising:
performing, by a radiation imaging unit, radiation imaging and generating radiation image data based on detected radiation;
performing, by an image processing unit, first image processing on the radiation image data to generate a first image and transmitting the first image to an information terminal;
subjecting, by the radiation imaging unit, the radiation image data to second image processing to generate a second image;
awaiting, by the radiation imaging unit, a notification of completion of the radiation imaging from the information terminal; and
transmitting, by the radiation imaging unit, the second image to the information terminal in a case where the radiation imaging unit does not receive the notification from the information terminal after starting transmission of the radiation image data to the image processing unit.

17. A radiographic imaging apparatus, comprising:
at least one memory storing instructions; and
at least one processor that, when executing the instructions, causes the radiographic imaging apparatus to:
perform radiation imaging and generate radiation image data based on detected radiation;
subject the radiation image data to second image processing to generate a second image and transmit the second image to an information terminal;
await a notification of completion of the radiation imaging from the information terminal; and
transmit the second image to the information terminal in a case where the radiographic imaging apparatus does not receive the notification from the information terminal after starting transmission of the radiation image data to an image processing unit performing first image processing on the radiation image data to generate a first image and capable of transmitting the first image to the information terminal.

18. The radiographic imaging apparatus according to claim 17, wherein the at least one processor, when executing the instructions, further causes the radiographic imaging apparatus to perform at least one of cancelling the second image processing and discarding the second image in a case where the radiographic imaging apparatus receives the notification from the information terminal after starting the transmission of the radiation image data to the image processing unit.

19. The radiographic imaging apparatus according to claim 17, wherein the at least one processor, when executing the instructions, further causes the radiographic imaging apparatus to check whether the second image processing has been completed in a case where the radiographic imaging apparatus has not received the notification, and
in a case where the second image processing has been completed, transmits the second image to the information terminal.

* * * * *